(12) United States Patent
Fellows

(10) Patent No.: US 6,281,498 B1
(45) Date of Patent: Aug. 28, 2001

(54) INFRARED MEASURING GAUGES

(75) Inventor: Timothy Gordon Fellows, Cirencester (GB)

(73) Assignee: Infrared Engineering Limited (GB)

( * ) Notice: Subject to any disclaimer, the term of this patent is extended or adjusted under 35 U.S.C. 154(b) by 0 days.

(21) Appl. No.: 09/308,412

(22) PCT Filed: Nov. 19, 1997

(86) PCT No.: PCT/GB97/03176
§ 371 Date: May 19, 1999
§ 102(e) Date: May 19, 1999

(87) PCT Pub. No.: WO98/22806
PCT Pub. Date: May 28, 1998

(30) Foreign Application Priority Data

Nov. 19, 1996 (GB) ................................................. 9624035

(51) Int. Cl.[7] ........................... G01N 21/35; G01N 21/31
(52) U.S. Cl. ................................ 250/339.06; 250/339.1; 250/339.12; 250/339.01
(58) Field of Search .................... 250/339.06, 339.1, 250/339.09, 339.11, 559.27, 339.12, 341.8, 340, 339.01

(56) References Cited

U.S. PATENT DOCUMENTS 3,551,678 * 12/1970 Mitchell .............................. 250/339.1

(List continued on next page.)

FOREIGN PATENT DOCUMENTS

| 0518393 | 12/1992 | (EP) . |
| WO 93/06460 A1 | * 4/1993 | (WO) .............................. G01N/21/35 |

OTHER PUBLICATIONS

Patent Abstracts of Japan, vol. 014, No. 337, (P–1079) Jul. 20, 1990 & JP 02 115750 A (Yokogawa Electric Corp), Apr. 27, 1990, see Abstract.

*Primary Examiner*—Constantine Hannaher
*Assistant Examiner*—Albert Gagliardi
(74) *Attorney, Agent, or Firm*—Miles & Stockbridge P.C.; Edward J. Kondracki

(57) ABSTRACT

An infrared gauge for, and a method of, measuring a parameter of a sample, e.g. moisture content or sample thickness, the gauge comprising:

a source of infrared radiation directed at the sample, a detector for detecting the amount of infrared radiation transmitted, scattered or reflected from the sample at at least one measuring wavelength and at at least one reference wavelength, wherein the parameter absorbs infrared radiation at the at least one measuring wavelength and absorbs a lesser amount of infrared radiation at the at least one reference wavelength, and an algorithm processing unit for calculating the value of the parameter of interest from the intensity of radiation detected by the detector at the measuring and the reference wavelengths, the value of the parameter of interest being calculated according to the following equation:

$$P = \frac{a_0 + \sum a_i f(S_i)}{b_0 + \sum b_i f(S_i)} + c_0$$

where:

P is the predicted value of the parameter concerned, for example film thickness or moisture content;

$a_0$, $b_0$ and $c_0$ are constants;

i is 1, 2, 3 . . . and denotes the different wavelengths used;

$S_i$ is the signal produced when the sample is exposed to a given wavelength i;

$a_i$ and $b_i$ are constants; and $f(S_i)$ stands for a transformation applied to the signal $S_i$.

This provides improved accuracy of measuring the parameter.

6 Claims, 4 Drawing Sheets

U.S. PATENT DOCUMENTS

| | | | | |
|---|---|---|---|---|
| 4,006,358 | * | 2/1977 | Howarth | 250/339.1 |
| 4,260,262 | | 4/1981 | Webster . | |
| 4,300,049 | * | 11/1981 | Sturm | 250/339.09 |
| 4,310,763 | * | 1/1982 | Shields | 250/339.1 |
| 4,577,104 | * | 3/1986 | Sturm | 250/339.1 |
| 5,250,811 | * | 10/1993 | Lippert et al. | 250/339.09 |

\* cited by examiner

INFRARED MEASURING GAUGES

The present invention relates to infrared absorption gauges and in particular to the analysis of signals produced from such gauges to measure a parameter of a sample under investigation.

Infrared absorption gauges are well-known and used for example for measuring constituents of samples (e.g. the moisture content of paper or tobacco, or the fat, protein and water contents of foodstuffs), the amounts of substances absorbed or adsorbed on a substrate, the thickness of coatings or films on a substrate or the degree of cure of resins in a printed circuit board. In this specification, the term "parameter" is used to denote the property (composition, coating thickness etc.) of the sample being measured.

Infrared absorption gauges operate by projecting infrared radiation at two or more wavelengths onto a sample or substrate and measuring the intensity of radiation reflected, transmitted or scattered by the sample. Signals proportional to the measured intensity are processed to provide a value of the parameter being measured. At least one of the two more wavelengths projected by the gauge is chosen to be absorbed by the parameter of interest while the other wavelength is chosen to be substantially unaffected by the parameter of interest. For example, when measuring the amount of water in a sample, one of the wavelengths (the "measuring wavelength") can be chosen at an absorption wavelength of water (either 1.45 micrometre or 1.94 micrometre) and the other wavelength (known as the "reference wavelength") is not significantly absorbed by water.

Generally, gauges include an infrared radiation source having a broad emission spectrum and a detector for receiving radiation reflected, scattered or transmitted by the sample; filters are placed between the source and the sample to expose the sample only to the desired measuring and reference wavelengths; in this case, the sample is successively exposed to radiation at the selected wavelengths, e.g. by placing appropriate filters on a rotating wheel in front of the radiation source. Alternatively (but less preferably), the filters can be placed between the sample and the detector and each filter is successively interposed between the sample and the detector. Naturally, if the source can produce radiation of the desired wavelength without the use of filters, then such filters can be dispensed with.

The detector measures the intensity of light after interaction with the sample and produces a signal according to the intensity of the radiation incident upon it. In the most simple case, by calculating the ratio between the signal from the detector when receiving light at the measuring wavelength to that when receiving light at the reference wavelength, a signal can be obtained that provides a measure of the parameter concerned, for example the amount of moisture in a sample. Often, several measuring wavelengths and/or several reference wavelengths are used and the signals of the measuring wavelengths and of the reference wavelengths are used to calculate the parameter concerned.

In fact, conventionally, the value of the parameter is calculated according to the following algorithm (I):

$$P = a_0 + \sum_{i=1}^{n} a_i \log S_i$$

where:
is the predicted value of the parameter concerned, for example film thickness or moisture content;
$a_o$ is a constant;
i is 1, 2, 3 . . . and denotes the different wavelengths used;
n is the number of wavelengths used in the gauge;
$S_i$ is the signal produced when the sample is exposed to a given wavelength i; and
$a_i$ is a constant to be applied to signal $S_i$.

The above formula can be derived from the Beer-Lambert law for non-scattering materials. The base of the logarithms in the above algorithm is immaterial because the value of the constants $a_i$ can be scaled according to the basis of the logarithm used.

The constants $a_o$ and $a_i$ can be calculated from a so-called "calibration" set of data, which is a set of infrared absorption data from a range of samples whose parameter of interest is known (so-called "reference samples"); thus by measuring the signals produced when each of the reference samples is exposed at each wavelength, the constants $a_o$ and $a_i$ can be calculated by solving a straightforward set of simultaneous equations. It is possible to simplify the calculation by applying a constraint that the sum of the constants $a_i$ should equal zero. In fact, it is exceedingly unlikely that a single set of constants $a_0$ and $a_i$ will produce an exact fit across the whole range of parameter values and therefore the constants $a_0$ and $a_i$ are calculated to produce the "best fit" to the data obtained in the calibration set, for example the constants are set to give the minimum residual standard deviation (rsd) for the data concerned. The calibration set of data should be obtained from samples having parameters across the whole range of parameters that will, in practice, be encountered when using the infrared gauge.

It will be appreciated that the accuracy of the infrared gauge can be improved by increasing the number of wavelengths that the gauge uses. However, this greatly adds to the expense, complexity and response time of the gauge and accordingly it is desirable to provide an alternative method for improving the accuracy of infrared gauges.

We have found that it is possible to greatly improve the accuracy of an infrared gauge by the use of a new algorithm (II) as follows:

$$P = \frac{a_0 + \sum a_i f(S_i)}{b_0 + \sum b_i f(S_i)} + c_0$$

where:
P is the predicted value of the parameter concerned, for example film thickness or moisture content;
$a_0$ $b_0$ and $c_0$ are constants;
i is 1, 2, 3 . . . and denotes the different wavelengths used;
n is the number of wavelengths used in the gauge;
$S_i$ is the signal produced when the sample is exposed to a given wavelength i;
$a_i$ and $b_i$ are constants; and
$f(S_i)$ stands for a transformation applied to the signal $S_i$; this transformation could be a log function, log (1/S) or, indeed, the transformation could be an identity transformation, i.e. no transformation at all). In the latter case, the algorithm would be algorithm (III):

$$P = \frac{a_0 + \sum a_i S_i}{b_0 + \sum b_i S_i} + c_0$$

In the algorithm of the present invention, it is not necessary to use all the signals to calculate the numerator or the denominator, in which case the value of any constant $a_i$ or $b_i$ would be set at zero.

According to one aspect of the present invention, there is provided an infra red gauge for measuring a parameter of a sample, the gauge comprising:

a source of infrared radiation directed at the sample, a detector for detecting the amount of infrared radiation transmitted, scattered or reflected from the sample at at least one measuring wavelength and at at least one reference wavelength, wherein the parameter absorbs infrared radiation at the said at least one measuring wavelength and absorbs a lesser amount of infrared radiation at the said at least one reference wavelength, means for calculating the value of the parameter of interest from the intensity of radiation detected by the detector at the measuring and the reference wavelengths, the value of the parameter of interest being calculated according to the following equation:

$$P = \frac{a_0 + \sum a_i f(S_i)}{b_0 + \sum b_i f(S_i)} + c_0$$

where:

P is the predicted value of the parameter concerned, for example film thickness or moisture content;

$a_0$, $b_0$ and $c_0$ are constants;

i is 1, 2, 3 . . . and denotes the different wavelengths used;

$S_i$ is the signal produced when the sample is exposed to a given wavelength i;

$a_i$ and $b_i$ are constants; and $f(S_i)$ stands for a transformation applied to the signal $S_i$.

According to another aspect of the present invention there is provided a method of measuring the value of a parameter in a sample, the method comprising:

directing infrared radiation at the sample, measuring the intensity of infrared radiation reflected, scattered or transmitted by the sample at at least a first wavelength (measuring wavelength) and at at least a second wavelength (reference wavelength), the parameter absorbing infrared radiation at the said measuring wavelength(s) and being less absorbing at the said reference wavelength(s), and calculating the value of the parameter of interest from the intensity of radiation detected by the detector at the measuring and the reference wavelengths, the value of the parameter of interest being calculated according to the following equation:

$$P = \frac{a_0 + \sum a_i f(S_i)}{b_0 + \sum b_i f(S_i)} + c_0$$

where:

P is the predicted value of the parameter concerned, for example film thickness or moisture content;

$a_0$, $b_0$ and $c_0$ are constants;

i is 1, 2, 3 . . . and denotes the different wavelengths used;

$S_i$ is the signal produced when the sample is exposed to a given wavelength i;

$a_i$ and $b_i$ are constants to be applied to signal $S_i$; and $f(S_i)$ stands for a transformation applied to the signal $S_i$.

Our current understanding of the benefits obtained from using Algorithms (II) and (III) are that the numerator part of the algorithm provides a prediction of the parameter of interest, but, as with conventional algorithms, shows different measurement sensitivities for materials where the mean effective path length of light through the material can vary. The effect can occur, for example, where the light scattering characteristics of the material varies, or, the thickness of the material varies independently to the parameter of interest. The purpose of the denominator in the algorithm is then to compensate for factors which affect the measurement sensitivity.

A simple example is in the measurement of percentage moisture in paper, where the mass per unit area of the base material is not constant. The numerator would produce values proportional to the total mass of water content observed, and the denominator would produce values proportional to the corresponding total mass of the base material observed.

It is difficult to calculate the optimum constants used in algorithms II and III by theoretical methods and therefore an empirical method is usually necessary, whereby an iterative numerical procedure is used to fit, constants when a calibration data set of samples with known parameter values, is employed.

The invention will now be described further, by way of example, with reference to the accompanying drawings, in which.

Figure 1:
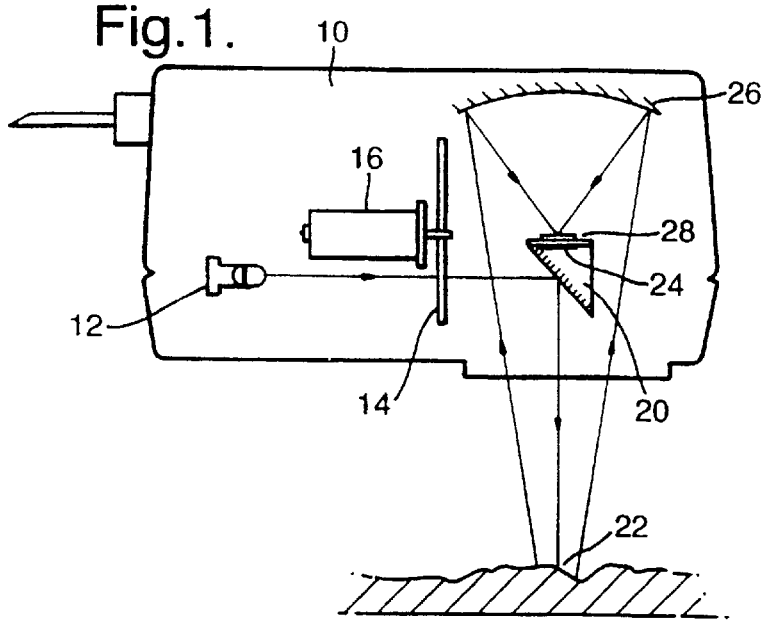
FIG. 1 is a schematic section through the head of an infrared gauge according to the present invention.
Figure 2:
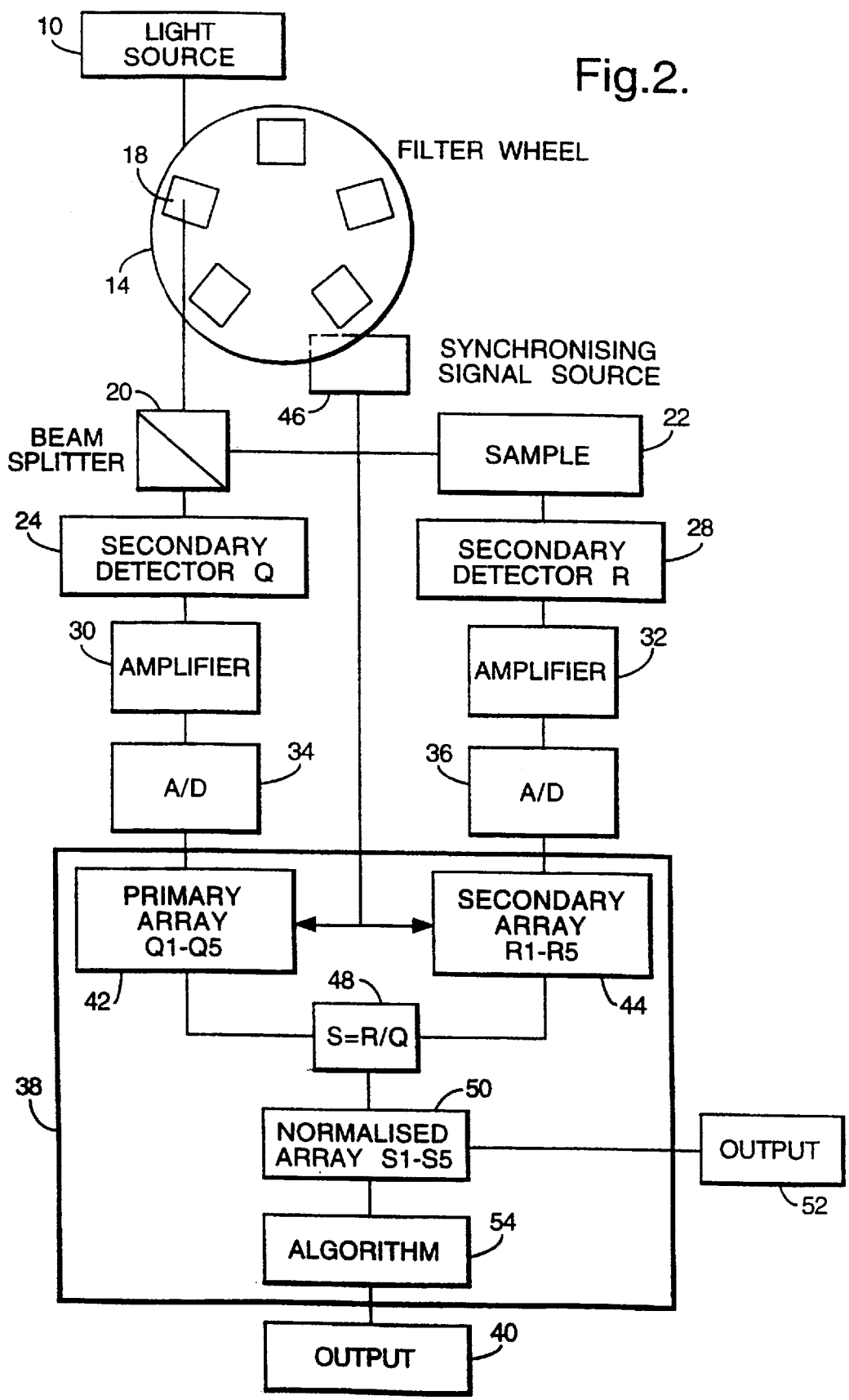
FIG. 2 is a schematic block diagram of the circuitry of the infrared gauge according to the present invention.

Referring initially to FIGS. 1 and 2, FIG. 1 shows the head 10 of an infrared gauge according to the present invention. The head 10 contains a lamp 12 providing a source of infrared radiation, a broad emission spectrum and a circular filter wheel 14 driven by a motor 16.

The filter wheel 14, further illustrated in FIG. 2, carries a series of filters 18, in this instance five such filters. Each filter 18 is designed to pass a different selected emission wavelength.

Light passed by a respective filter 18 is arranged to strike a beam splitter 20 which reflects a portion of the light beam downwardly out of the infrared gauge 10 towards a sample 22. A remaining portion of the infrared light beam striking the beam splitter 20 is refracted within the beam splitter towards a primary detector 24 in the form of a photo-electric sensor. Meanwhile, the light emitted by the head 10 towards the sample 22 is reflected back from the sample 22 towards a collecting mirror 26 in the head 10 and thence to a secondary detector 28 in the form of another photo-electric sensor. The two detectors 24, 28 thus generate detection signals representing, respectively, the intensity of the light emitted by the lamp 12 and filtered by a selected one of the filters 18, and the intensity of that same light after reflection from the sample 22. The detection signals in the present instance are voltage signals.

Referring to FIG. 2, the voltages output by the detectors 24, 28 in use are first amplified by respective amplifiers 30, 32 and then converted into binary form by respective A/D converters 34, 36. The binary signals output by the A/D converters 34, 36 are both supplied to a central processing unit (CPU) 38, to be described in greater detail below, for generating at a main output 40 a signal representing the parameter concerned.

Before the infrared gauge can be used to measure a parameter in the sample 22, however, it is necessary to locate one or more measuring wavelengths and reference wavelengths. This is usually accomplished by taking infrared spectra of various samples, employing for example a spectrophotometer, and locating (a) those wavelengths which vary strongly with any variation in the parameter of interest to locate the measuring wavelengths and (b) those wavelengths which vary only weakly (or not at all) with any variation in the parameter of interest to locate the reference wavelengths. After the required wavelengths have been selected, the appropriate filters 18 are incorporated into the filter wheel 14 of the infrared gauge of head 10.

A "calibration" set of values is then used in the described infrared gauge to calculate the value of the constants $a_0$, $b_0$, $a_i$ and $b_i$ in algorithm (II) above. This involves the taking of a large number of samples whose parameter is of a known value. It will be appreciated that the number of samples required will increase with the number of wavelengths used and it is estimated that at least forty samples should be used to compile the calibration set when three wavelengths are measured in the gauge, seventy samples should be used when four wavelengths are used in the gauge, and a hundred samples should be used when five wavelengths are used in the gauge. The voltage signals generated by the detectors 24, 28 at each wavelength for each sample are then used to calculate the constants in algorithm (II) of the present invention using the methods and software described below.

For each such sample whose parameter is of a known value, the sample is placed under the infrared gauge head 10 and for each respective filter 18 voltage, signals are supplied from the detectors 24, 28 to the CPU 38. The signals Q1 to Q5 obtained from the primary detector 24 after amplification and A/D conversion are stored in a FIFO memory array 42, and the corresponding signals RI to R5 obtained from the secondary detector 28 are stored in a FIFO memory array 44.

Entry of the binary values from the two detectors 24, 28 into the two memory arrays 42, 44 is synchronised by means of a synchronising signal source 46 shown schematically in FIG. 2. Essentially, this synchronising signal source 46 comprises a photo-electric emitter and photo-electric sensor positioned on opposite sides of the filter wheel 14 just inside its circumference. The filter wheel 14 itself has a series of small holes formed at a constant angular spacing throughout the extent of its circumference, with the exception that at one point of the circumference two of the holes are positioned closely adjacent one another at a significantly reduced angular spacing. A control unit within the synchronising signal source 46 drives the motor 16 and monitors the passage of the two closely adjacent holes and then the number of holes that subsequently pass the photo-electric emitter to provide an indication as to which filter 18 is in front of the light source 10 and to ensure that the binary signals are stored in the arrays 42, 44 in respective storage locations corresponding to each filter 18.

Once binary signals corresponding to each of the filters 18 have been stored in the memory arrays 42, 44 for any particular sample whose parameter is of a known value, then signals SI to S5 are calculated from these binary values in an arithmetic control unit 48 and are subsequently stored in a further memory array 50. The signal S in each case is derived in the arithmetic unit 48 by dividing the binary value R obtained from the secondary detector 28 by the corresponding binary value Q obtained from the primary detector 24. In the example illustrated, there are five filters 18 and, therefore, there will be five values S1 to S5 eventually stored in the memory array 50. At this stage, these values are supplied to a secondary output 52 for calculation of the constants $a_o$, $b_o$, $a_i$ and $b_i$ by comparing the measured values S1 to S5 from each sample whose parameter is known with the known value for that parameter.

Several suitable numerical procedures are known for determining constants, $a_o$, $b_o$, $a_i$ and $b_i$, of which some are available in the form of computer software. Such methods include the "steepest descent" method, the "inverse-Hessian" method, the "Levenberg-Marquardt" method and the "full Newtonian" method. These methods are fully described in "Numerical Recipes in C" by Press, Teukonsky, Vetterling & Flannery (published by Cambridge University Press).

The full Newtonian method is the most complex and gives the most reliable results but it requires a large computing capacity and takes a long time to arrive at values for the constants. Accordingly, we prefer to use the "steepest descent" or the "Levenberg-Marquardt" methods.

Levenberg-Marquardt software is commercially available in the following computer packages:

1) LabVIEW produced by National Instruments Corporation of 6504 Bridge Point Parkway, Austin, Tex. 78730-5039, USA or
2) Statgraphics produced by STSC Inc., 2115 East Jefferson Street, Rockville, Md. 20852, USA; and
3) "Numerical Recipes in C" (software routines can be purchased with the book of the same title mentioned above).

Figure 3:
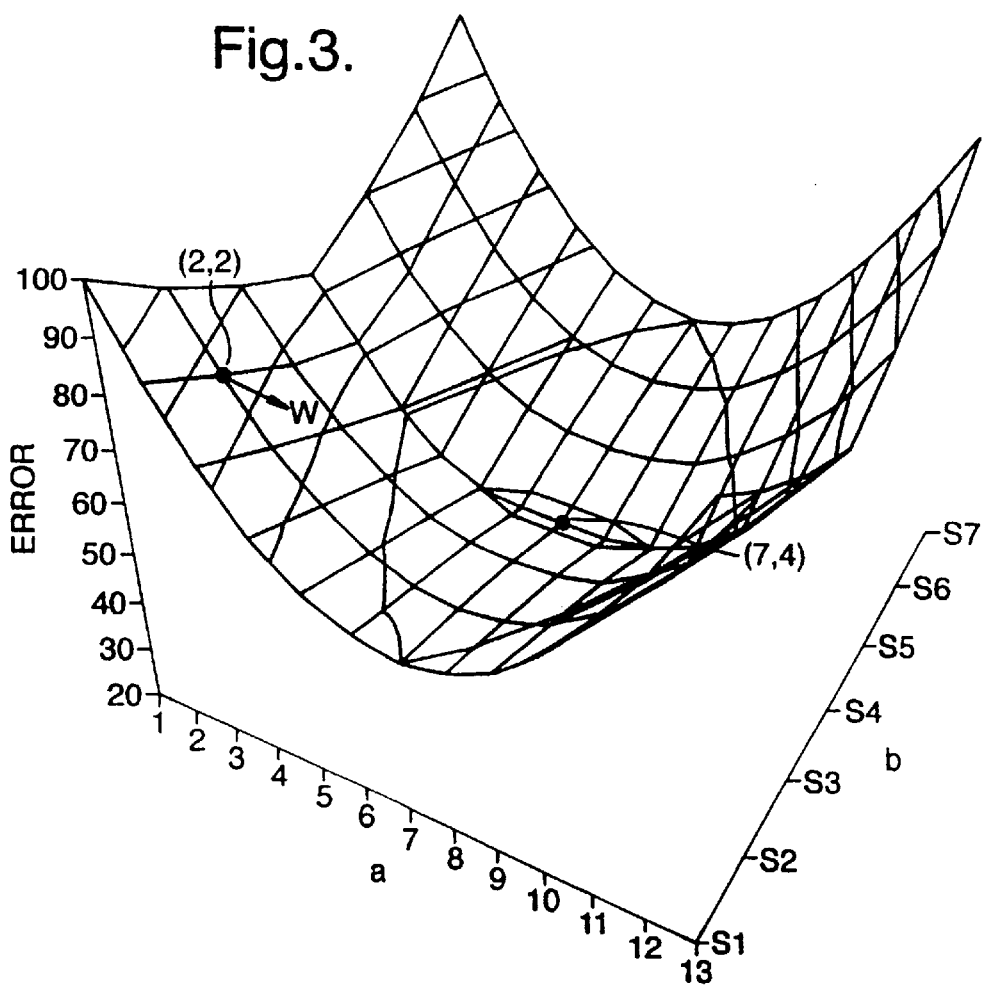
FIG. 3 is a diagrams for illustrating the selection of the constants in one particular example according to the present invention.

It is not necessary to describe precisely how the above computer packages calculate the constants but it can be visualised in the case of a simplified version of algorithm II that contains only two constants, $a_1$ and $b_1$: the values of $a_1$ and $b_1$ for a given sample could be plotted along X and Y axes and the "accuracy" of the value P calculated from algorithm II for the different values of $a_1$ and $b_1$ could be plotted along the Z axis; the "accuracy" plotted along the Z axis would be the difference between the value of P calculated from solving the algorithm and the actual value of the parameter in the sample. The resulting plot would be a three-dimensional surface and the desired values of $a_1$ and $b_1$ would be those where the plot had a minimum, i.e. where the accuracy is greatest (or the deviation from the value of the actual parameter is the least). An example of such a plot is shown in FIG. 3.

The easiest to visualise of the above-described methods for calculating the "best fit" values of the constants (i.e. the values of the constants that minimises the difference between the calculated value of the parameter P and the value of the actual parameter in the sample) is the "steepest descent" method. Applying that method to find the minima in the plot described in the previous paragraph, a pair of values for the two constants $a_1$ and $b_1$ is initially selected as a "guestimate"; (a=2, b=2, in FIG. 3) the steepest gradient of the plot at the point corresponding to the initial values of $a_1$ and $b_1$ is calculated (shown by arrow W in FIG. 3). The direction of the steepest gradient with the plot gives after a pre-determined distance two new values for $a_1$ and $b_1$. The steepest gradient of the plot at the point corresponding to the new values of $a_1$ and $b_1$ is then calculated and the direction of the steepest gradient with the plot gives two further values for $a_1$ and $b_1$. This process is repeated until the desired minimum is reached (a=7, b=4 in FIG. 3).

The Levenberg Marquardt method also uses an iterative process but instead estimates, from the shape of the plot at a given pair of constants $a_1$ and $b_1$ where the minimum is likely to be. It then performs a similar operation at the point of the plot where the minimum was predicted to be; this procedure is continued until the actual minimum is located. The Levenberg Marquardt method generally uses a fewer number of iterative steps and is therefore to be preferred.

It will be appreciated that the plot may have several local minima and it may well be necessary to validate that any minimum found is in fact the true minimum of the plot by repeating the iterative process from several starting values of the constants $a_1$ and $b_1$ concerned.

The above graphical representation of the plot is a vast over-simplification of the actual calculation of the constants in algorithm II since many more than two constants will be present and hence the "plot" will have more than 3 dimensions.

At this point, it should be mentioned that the LabVIEW package mentioned above contains a univariate routine which will have to be modified to make it multi-variate before it can applied to the calculation of the constants. However, the Statgraphics package mentioned above is multi-variate and therefore no such modification is required.

Once the constants have been determined from the calibration set of samples using one of the procedures described above, then a processing unit 54 in the CPU 38 is set up to perform algorithm (II) using these constants.

After this, a further set of samples is then used to ensure that the overall readings given by the gauge are accurate; this is the so-called "validation set" of samples. The parameter of interest is also known for these samples and the value P is calculated in processing unit 54 from algorithm (II) from the signals S1 to S5 obtained by submitting these samples to measurement by the infrared gauge. Obviously, if the values of the parameter obtained at output 40 from the samples in the validation set do not comply with the known values to an acceptable degree of accuracy, then the calibration step must be repeated.

After validation, the infrared gauge incorporating the algorithm of the present invention can be used to predict from the signals produced by the infrared radiation detectors 24, 28 of the gauge the parameter of interest, for example polymer film thickness or water content in paper or fat content in meat, and to supply such parameter to main output 40

It is well-known that infrared gauges can measure either the infrared light transmitted by a sample or the infrared light reflected or scattered from a sample. The algorithm of the present invention is applicable to all such methods.

The parameters that can be measured according to the present invention include not only the proportion of a given substance in a material (for example the percentage moisture content in paper or the percentage fat content in meat) but also the thickness of a coating on a material (for example the thickness of adhesive on a paper substrate).

It will be appreciated that the algorithm according to the present invention can be incorporated into a more complex algorithm having the same general effect as algorithm (II). The present invention also extends to the use of such more complex algorithms.

The use of the algorithms of the present invention are particularly beneficial when measuring highly scattering substrates, particularly paper.

Example 1

The diffuse reflectant infrared spectra of 37 widely-varying types of paper, each having 10 different moisture content levels in the range 3.5 to 9.5%, were collected. The actual moisture content of these papers (so called "reference values") were obtained using an oven reference technique by which the moisture-containing paper is weighed, it is then placed in an oven to dry out, and the dried paper is then weighed again. From the change in the weight of paper, the initial moisture content can be calculated.

The papers used ranged in weight from 40 to 400 g per square metre and included glassine, mechanical paper, Kraft paper and chemical paper of different types. From an analysis of the spectra, various wavelengths were selected for use in a gauge. The Applicants have developed computer software that simulates the response of a gauge containing interference filters centred on two or more wavelengths of the spectrum that look promising. The simulation convolves the spectrum over each selected wavelength with a 1.6% bandwidth gaussian function to simulate the effect, in the gauge, of the use of an optical interference filter with a "full width, half maximum" bandwidth of 1.6% of the centre wavelength. The computer software can also calculate the values of the constants $a_0$, $b_0$, $c_0$, $a_i$ and $b_i$ in algorithm (II) above for the sample concerned for a set of selective combinations of wavelengths. From these constants, it is possible to estimate the accuracy of the measurement on the paper samples for each combination of wavelengths to locate an optimum set of filters for use in the gauge. Using this simulation technique, five wavelengths were selected at 1817, 1862, 1940, 2096 and 2225 nm. However, it is not necessary to select the wavelengths using such a simulation technique and the wavelengths can be selected merely by examining the spectra of the samples and choosing appropriate measuring and reference wavelengths.

Optical interference filters centred on the above five wavelengths were incorporated into an infrared gauge and a calibration set of data was obtained. From this, the constants as, $b_0$, $c_0$, $a_i$ and $b_i$ in algorithm (II) above (in which $f(S_i)=\log S_i$) or algorithm III were calculated and the accuracy of the algorithm to predict the actual values of the parameter in the reference samples was calculated. The results were expressed as the percentage of moisture in the various samples falling within one standard deviation of the value predicted from the algorithm. The results were as follows:

| | |
|---|---|
| conventional algorithm (I) | 0.507% |
| algorithm (II), where $f(S_i) = \log S_i$ | 0.331% |
| algorithm (III) | 0.335% |

These improvements could not be achieved using conventional algorithm I and simply increasing the number of measurement wavelengths used in a gauge. For example, when using twelve different wavelengths in a conventional algorithm, an accuracy of only 0.44% moisture to one standard deviation was observed.

Example 2

The infrared spectra of 37 different types of paper, each at 10 different moisture levels between 1% and 10% wet weight moisture, were measured in a diffuse reflectance spectrophotometer. By examination of the spectral data and from information published, five suitable measurement wavelengths were selected. These were as follows: 1.7 micrometres (first neutral reference), 1.8 micrometres (second neutral reference), 1.94 micrometres (water absorption band), 2.1 micrometres (cellulose absorption band), and 2.2 micrometres (third neutral reference). Optical interference filters centred at these wavelengths were manufactured and fitted into the filter wheel 14 of an infrared absorption gauge as detailed earlier.

In this example, a set of 6 paper samples, with a wide range of weight per unit area, were selected to include in a calibration set. Each sample was presented to the gauge at several different moisture contents, and the signals, S1 to S5, were recorded. The weight of each sample was measured at the time of signal recording, and subsequently the actual % moisture content (so called "reference values") of these samples were calculated by drying them completely in an electric oven and calculating the weight loss as a percentage of the wet weight.

The applicants then employed computer software based on LabVIEW, which incorporates an iteration routine described earlier, to determine the optimum values of constants $a_0$, $b_0$, $c_0$, $a_i$ and $b_i$ for algorithm (I) and (II) in order to predict the parameter of interest from the infrared gauge signals S1 to S5. In this example, the gauge signal data and the corresponding reference values were used in the software to calculate the optimum constants for algorithm (II) to predict percentage moisture. Various combinations of between 2 and 5 filter signals were tested in the numerator and in the denominator part of the algorithm. The best results were as follows:

| Constant | Filter wavelength (micrometers) | Constant Value |
|---|---|---|
| $a_1$ | 2.2 | 0 |
| $a_2$ | 1.7 | 26 |
| $a_3$ | 1.8 | 0 |
| $a_4$ | 1.94 | −37 |
| $a_5$ | 2.1 | 11 |
| $a_0$ |  | 3 |
| $b_1$ | 2.2 | 0 |
| $b_2$ | 1.7 | −2.4 |
| $b_3$ | 1.8 | 5.3 |
| $b_4$ | 1.94 | 0 |
| $b_5$ | 2.1 | −2.9 |
| $b_0$ |  | 1 |
| $c_0$ |  | 0.75 |

Figure 4:
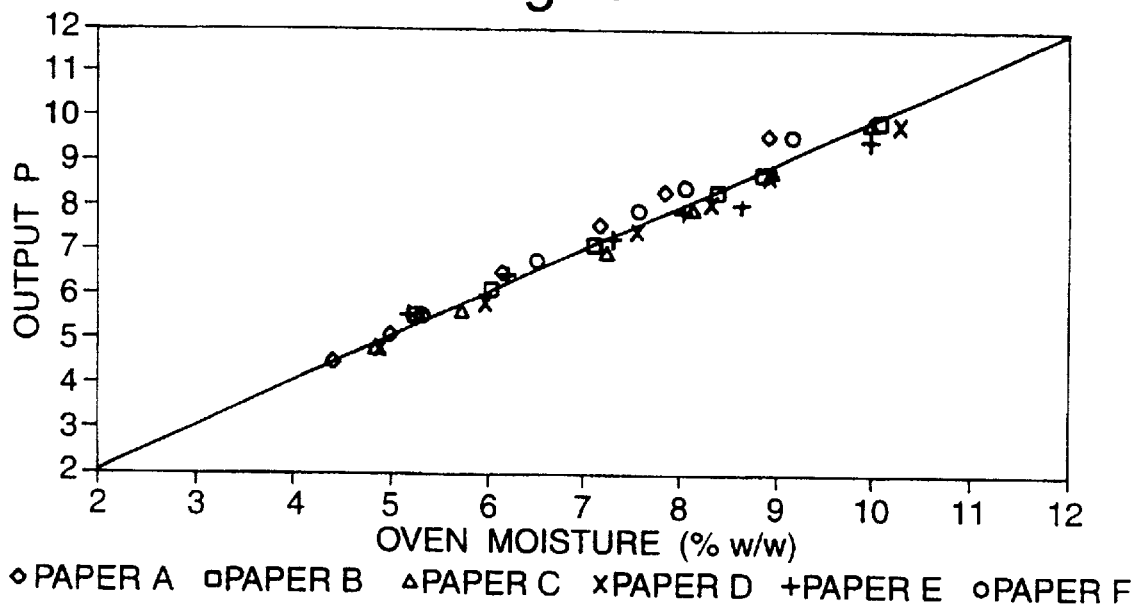
FIGS. 4 to 7 are graphs representing a particular worked example of the present invention.

These constants gave a standard error value of 0.288% and a correlation coefficient of 0.986. An XY graph of these is shown in FIG. 4.

Figure 5:
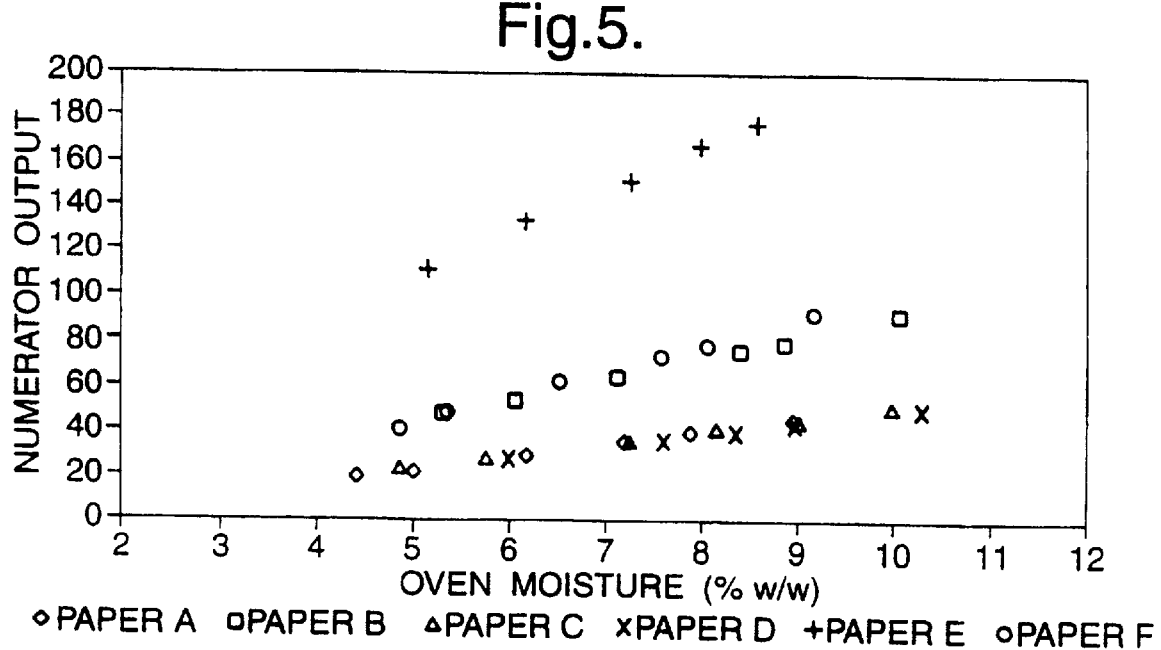

The numerator part of the algorithm without the denominator part compensating for the effect of different measurement sensitivities for the different papers, results in noticeably different slopes for different papers, depending upon the weight and type. This is shown graphically in FIG. 5.

Figure 6:
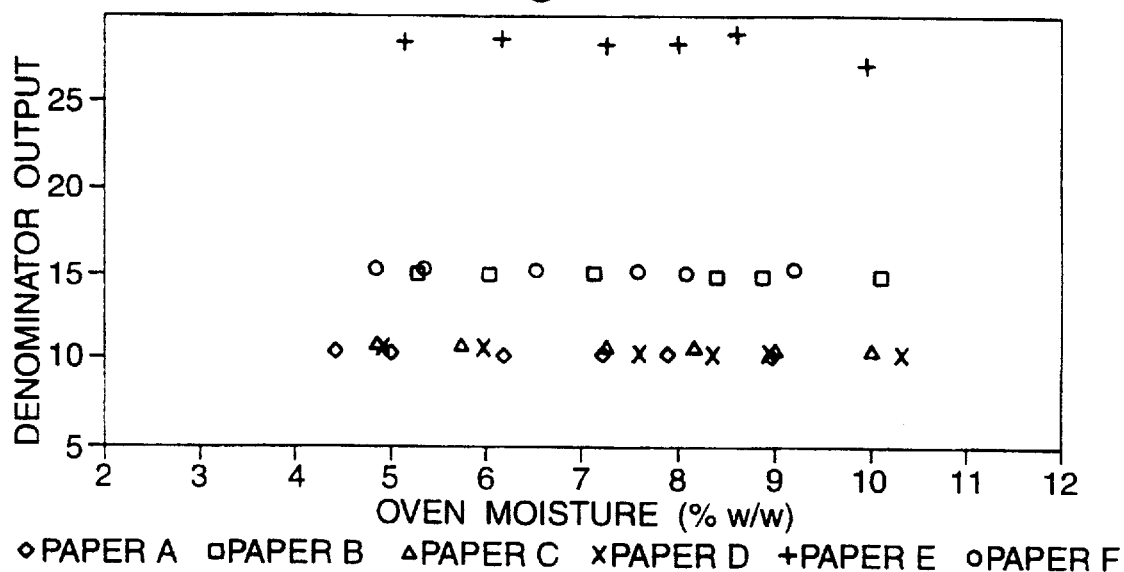

The compensating output of the denominator part of the algorithm is shown in FIG. 6. As shown, this part of the algorithm is not sensitive to variation in the paper moisture.

It is useful to compare the output P for a conventional Algorithm (I) and the output P for Algorithm (II), using the same filter wavelengths. The optimised constants for this example set of data using Algorithm (I) are given below:

| Constant | Filter wavelength (micrometers) | Constant value |
|---|---|---|
| $a_1$ | 2.2 | 0 |
| $a_2$ | 1.7 | 0.82 |
| $a_3$ | 1.8 | 0 |
| $a_4$ | 1.94 | −3.36 |
| $a_5$ | 2.1 | 2.54 |
| $a_0$ |  | 6.63 |

Figure 7:
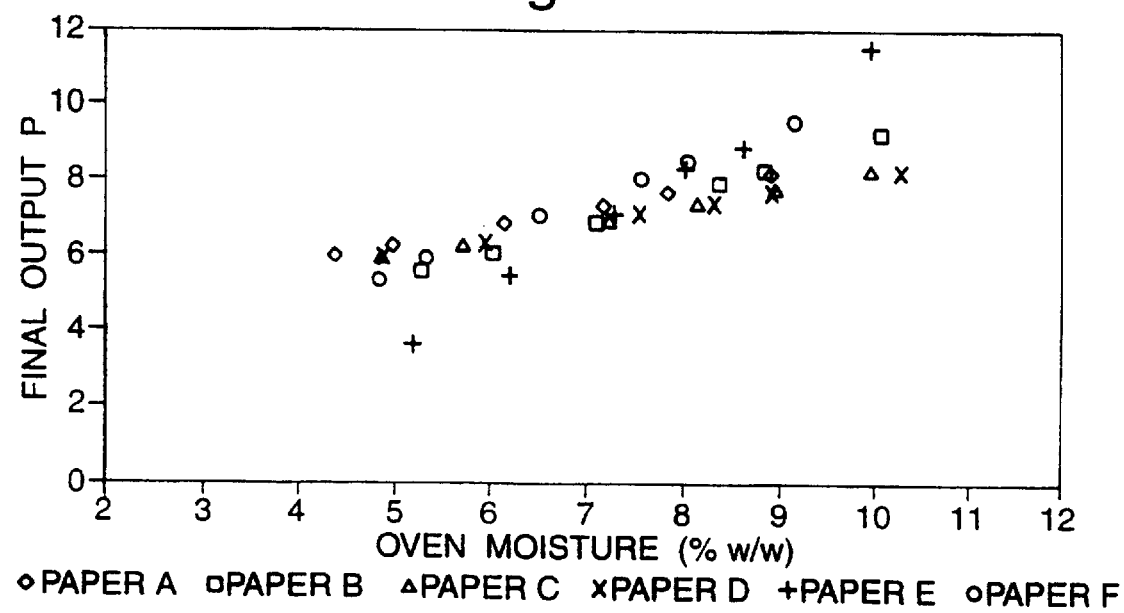

These constants gave a standard error value of 0.881% and a correlation coefficient of 0.866. An XY graph of these is shown in FIG. 7 below. It can be seen that, although the standard deviation of errors about the best-fit line are minimised, the different sensitivities to paper weight and type remain.

What is claimed is:

1. An infrared gauge for measuring a parameter of a sample, the gauge comprising:

a source of infrared radiation directed at the sample, a detector for detecting the amount of infrared radiation transmitted, scattered or reflected from the sample at at least one measuring wavelength and at at least one reference wavelength, wherein the parameter absorbs infrared radiation at the said at least one measuring wavelength and absorbs a lesser amount of infrared radiation at the said at least one reference wavelength, means for calculating the value of the parameter of interest from the intensity of radiation detected by the detector at the measuring and the reference wavelengths, the value of the parameter of interest being calculated according to the following equation:

$$P = \frac{a_0 + \sum a_i f(S_i)}{b_0 + \sum b_i f(S_i)} + c_0$$

where:

P is the predicted value of the parameter concerned, for example film thickness or moisture content;

$a_0$, $b_0$ and $c_0$ are constants;

i is 1, 2, 3 . . . and denotes the different wavelengths used;

$S_i$ is the signal produced when the sample is exposed to a given wavelength i;

$a_i$ and $b_i$ are constants; and $f(S_i)$ stands for a transformation applied to the signal $S_i$.

2. A gauge as claimed in claim 1, wherein the function f(S) is a log function or a log (1/S) function.

3. A gauge as claimed in claim 1, wherein the algorithm is an algorithm (III):

$$P = \frac{a_0 + \sum a_i S_i}{b_0 + \sum b_i S_i} + c_0.$$

4. A method of measuring the value of a parameter in a sample, the method comprising:

directing infrared radiation at the sample, measuring the intensity of infrared radiation reflected, scattered or transmitted by the sample at at least a first wavelength (measuring wavelength) and at at least a second wavelength (reference wavelength), the parameter absorbing infrared radiation at the said measuring wavelength(s) and being less absorbing at the said reference wavelength(s), and calculating the value of the parameter of interest from the intensity of radiation detected by the detector at the measuring and the reference wavelengths, the value of the parameter of interest being calculated according to the following equation:

$$P = \frac{a_0 + \sum a_i f(S_i)}{b_0 + \sum b_i f(S_i)} + c_0$$

where:

P is the predicted value of the parameter concerned, for example film thickness or moisture content;

$a_0$, $b_0$ and $c_0$ are constants;

i is 1, 2, 3 . . . and denotes the different wavelengths used;

$S_i$ is the signal produced when the sample is exposed to a given wavelength i;

$a_i$ and $b_i$ are constants to be applied to signal $S_i$; and $f(S_i)$ stands for a transformation applied to the signal $S_i$.

5. A method as claimed in claim 4, wherein the function $f(S_i)$ is a log function or a log $(1/S_i)$ function.

6. A method as claimed in claim 4, wherein the algorithm is an algorithm III $$P = \frac{a_0 + \sum a_i S_i}{b_0 + \sum b_i S_i} + c_0.$$

* * * * *